US005136078A

United States Patent [19]

Mitchell

[11] Patent Number: 5,136,078

[45] Date of Patent: Aug. 4, 1992

[54] SYNTHESIS OF B-CYANOHYDRINS

[75] Inventor: David Mitchell, Indianapolis, Ind.

[73] Assignee: Eli Lilly and Company, Indianapolis, Ind.

[21] Appl. No.: 661,278

[22] Filed: Feb. 26, 1991

[51] Int. Cl.[5] .................. C07C 253/16; C07D 333/12; C07D 333/16; C07D 307/42

[52] U.S. Cl. .................................... 558/347; 546/330; 548/205; 549/75; 549/491

[58] Field of Search ......................... 558/347; 546/330; 548/205; 549/75, 491

[56] References Cited

U.S. PATENT DOCUMENTS

| | | | |
|---|---|---|---|
| 2,364,422 | 12/1944 | Brooks | 558/347 |
| 2,453,062 | 11/1948 | Carpenter | 558/347 |
| 3,655,723 | 4/1972 | Drinkard, Jr. | 558/335 X |
| 4,314,081 | 2/1982 | Molloy et al. | 564/347 |
| 4,956,388 | 9/1990 | Robertson et al. | 514/651 |

FOREIGN PATENT DOCUMENTS 369685 5/1990 European Pat. Off. .

OTHER PUBLICATIONS

Migrdichian, The Chemistry of Organic Cyanogen Compounds, (1947), Reinhold Pub. Co., pp. 174–176.

Klunder, et al., *J. Org. Chem.*, 54, (1989); pp. 1295–1304.

Ko, et al., *J. Org. Chem.*, 52, (1987); pp. 667–671.

Liotta, et al., *Tetrahedron Letters*, 13, (1977); pp. 1117–1120.

Sugita, et al., *Chemistry Letters*, (1990); pp. 481–484.

Sassaman, et al., *J. Org. Chem.*, 55, (1990); pp. 2016–2018.

*Primary Examiner*—Joseph Paul Brust

*Attorney, Agent, or Firm*—Joseph A. Jones; Leroy Whitaker; Robert A. Conrad

[57] ABSTRACT

This invention provides a process for preparing 3-substituted-3-hydroxypropanenitriles.

6 Claims, No Drawings

SYNTHESIS OF B-CYANOHYDRINS

BACKGROUND OF THE INVENTION

3-Substituted-3-aryloxypropanamines are known in the art to be useful as medicinal agents by virtue of their action of inhibiting the reuptake of serotonin or norepinephrine. See, e.g., U.S. Pat. Nos. 4,314,081 and 4,956,388. The preferred characteristics of particular enantiomers over their racemates is also known—see, e.g., U.S. Pat. Nos. 4,956,388 and EPO Patent Application Publication 369,685.

This invention provides a method for converting an epoxide intermediate into a 3-substituted-3-hydroxypropanenitrile which can be used in the synthesis of the aforementioned pharmaceutical agents.

SUMMARY OF THE INVENTION

This invention provides a process for preparing a compound of Formula I

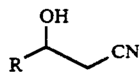

I wherein R is phenyl, $C_5$–$C_7$ cycloalkyl, thienyl, halothienyl, ($C_1$–$C_4$)alkylthienyl, furanyl, pyridyl, or thiazolyl, which comprises allowing an epoxide of the Formula II

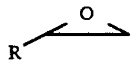

II to react with acetone cyanohydrin in the presence of a non-reactive organic base in an inert organic solvent.

DETAILED DESCRIPTION AND PREFERRED EMBODIMENT

The compounds of Formula I are intermediates for preparing 3-substituted-3-aryloxypropanamines as described in U.S. Pat. Nos. 4,314,081 and 4,956,388, which references are expressly incorporated into this specification. The intermediates of Formula I can be reacted with reagent of the formula Ar—Y where Y is a leaving group such as p-toluenesulfonyl, methanesulfonyl, triphenylphosphine oxide, halo, and the like and Ar is an optionally substituted phenyl or naphthyl group as described in the two cited U.S. patents. The resulting 3-substituted-3-aryloxypropanenitrile can then be reduced to the primary amine by standard methods and optionally alkylated to provide secondary or tertiary amines, all of which are medicinal agents as described in the cited patents. Alternatively, the intermediates of Formula I can be first reduced to the primary amine and then alkylated with Ar—Y as described above.

The preferred application of the process of this invention relates to those compounds wherein R is phenyl. Thus, in the preferred embodiment of this invention, the compound of Formula II is commercially available (R)-styrene oxide. Other related intermediates II are either commercially available or are prepared by literature methods.

The compounds of Formula I possess one chiral carbon atom, i.e., the atom to which the aryl and hydroxy groups are attached. The corresponding epoxide precursor II likewise has the same chiral atom. The reaction of this process is regio-selective in that the only product is the 3-substituted-3-hydroxypropanenitrile I with no 3-hydroxy-1-substituted-propanenitrile being observed. However, this reaction does not induce any stereoselectivity preferentially forming one of the enantiomers of Formula I. Thus, employing racemic epoxide II results in the formations of racemic I; employing a chiral epoxide II results in the formation of only the one corresponding enantiomer of Formula I.

The non-reactive organic bases employed in this invention are those which are soluble in the reaction mixture but do not react with the epoxide II, β-cyanohydrin I, or acetone cyanohydrin. Examples of such organic bases include trialkylamines, such as triethylamine, pyridine, and the like.

Suitable organic solvents are those which do not react with epoxide II, β-cyanohydrin I, or acetone cyanohydrin. Such solvents include haloalkanes, such as methylene chloride, 1,2-dichloroethane, and the like, and other solvents such as ethers (e.g., diethyl ether, tetrahydrofuran, dimethoxyethane), aromatics (e.g., benzene, toluene), and hydrocarbons (e.g., heptane, hexane, pentane, petroleum ether, and the like).

The reaction is best accomplished at temperatures above room temperature, particularly at temperatures from about 40° C. up to the reflux temperature of the reaction mixture.

The reaction is best carried out when there is an equivalent or slight molar excess of acetone cyanohydrin and organic base employed relative to the epoxide II. A preferred ratio would be at least about 10% molar excess of the acetone cyanohydrin and base relative to the epoxide reagent.

The process of this invention is also useful for the preparation of compounds where R is other than that defined earlier. For example, comparable compounds wherein R is $C_1$–$C_4$ alkyl, halo-substituted $C_1$–$C_4$ alkyl, $C_2$–$C_4$ alkenyl, various aryloxy-substituents, and the like can also be used in this transformation. In addition, epoxides wherein an additional substituent, such as alkyl group, is attached to the same carbon atom to which the R-group is attached can be successfully transformed into the corresponding beta-cyanohydrin. Thus, this process provides an effective means for preparing a variety of β-cyanohydrins beyond those specific R-substituents named earlier.

The advantage of the claimed process is the use of the organic reagent acetone cyanohydrin in place of conventionally employed alkali metal cyanides which can be quite toxic. In addition, the process as presently claimed provides the by-product acetone which is a volatile solvent that can be removed during the work-up of the reaction mixture and either disposed of or recycled in an environmentally sound manner.

The following experiments further illustrate the process of this invention. These examples are illustrative only are not intended to limit the scope of the invention.

EXPERIMENT 1

Preparation of (S)-3-phenyl-3-hydroxypropanenitrile

A mixture of 40.0 g of (R)-styrene oxide, 31.12 g of acetone cyanohydrin, 36.96 g of triethylamine, and 150 ml of tetrahydrofuran was heated at reflux for 18 hours. The reaction mixture was cooled, concentrated in vacuo, diluted with 200 ml of 2N potassium hydroxide, and extracted with diethyl ether. The ether extracts were combined, dried over magnesium sulfate, and concentrated in vacuo providing 34.3 g of the title intermediate.

IR (neat): 3445, 3065, 3034, 2899, 2255, 1604, 1495, 1456, 1412, 1329, 1204, 1087, 1058, 1028, 940, 868, 757, 703 $cm^{-1}$;

$^1H$ NMR (300 MHz, $CDCl_3$) $\delta$7.36 (m, 5H), 4.98 (t, J=6.11 Hz, 1H), 3.13 (br, s, 1H), 2.71 (d, J=6.09 Hz, 2H);

$^{13}C$ NMR (300 MHz, $CDCl_3$) $\delta$27.86, 69.87, 117.49, 125.59, 128.70, 128.87, 141.16;

Analysis for $C_9H_9NO$: Calc: C, 73.45; H, 6.16; N, 9.52; Found: C, 73.26; H, 6.20; N, 9.34.

EXPERIMENT 2

Preparation of 3-phenyl-3-hydroxypropanenitrile

The reaction of Experiment 1 was repeated with racemic styrene oxide on a 1.0 g (8.3 mmol) scale. The result was 1.1 g (88%) of racemic 3-phenyl-3-hydroxypropanenitrile.

IR (neat): 3445, 3065, 3034, 2899, 2255, 1604, 1495, 1456, 1412, 1329, 1204, 1087, 1058, 1028, 940, 868, 757, 703 $cm^{-1}$;

$^1H$ NMR (300 MHz, $CDCl_3$) $\delta$7.36 (m, 5H), 4.98 (t, J=6.11 Hz, 1H), 3.13 (br, s, 1H), 2.71 (d, J=6.09 Hz, 2H);

$^{13}C$ NMR (300 MHz, $CDCl_3$) $\delta$27.86, 69.87, 117.49, 125.59, 128.70, 128.87, 141.16;

Analysis for $C_9H_9NO$: Calc: C, 73.45; H, 6.16; N, 9.52; Found: C, 73.59; H, 6.33; N, 9.68.

EXPERIMENT 3

Experiment 2 was repeated using catalytic triethylamine (25% molar equivalent) with racemic styrene oxide on a 5.0 g (41.15 mmol) scale resulting in 5.34 g (87.6%) of the desired product.

I claim:

1. A regiospecific process for preparing a compound of Formula I

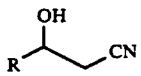

I wherein R is phenyl, $C_5$-$C_7$ cycloalkyl, thienyl, halothienyl, ($C_1$-$C_4$)alkylthienyl, furanyl, pyridyl, or thiazolyl, which comprises allowing an epoxide of the Formula II

O
R

II to react with acetone cyanohydrin in the presence of a trialkylamine in tetrahydrofuran.

2. The process of claim 1 wherein the trialkylamine is triethylamine.

3. The process of claim 1 wherein R is phenyl.

4. The process of claim 1 wherein the product is the regiospecific compound of formula

OH
R CN.

5. The process of claim 1 wherein the product is the regiospecific racemic mixture of formula OH OH
R CN and R CN.

6. A regiospecific process for preparing a compound of Formula I

OH
R CN

I wherein R is phenyl which comprises allowing an epoxide of the Formula II

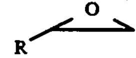

II to react with acetone cyanohydrin in the presence of triethylamine in tetrahydrofuran.

* * * * *